United States Patent [19]

Ramachandran et al.

[11] Patent Number: 5,109,124

[45] Date of Patent: Apr. 28, 1992

[54] NUCLEIC ACID PROBE LINKED TO A LABEL HAVING A TERMINAL CYSTEINE

[75] Inventors: Kuzhalmannam L. Ramachandran, Natick; Richard L. Cate, Plymouth, both of Mass.

[73] Assignee: Biogen, Inc., Cambridge, Mass.

[21] Appl. No.: 306,798

[22] Filed: Feb. 2, 1989

Related U.S. Application Data

[63] Continuation-in-part of Ser. No. 200,930, Jun. 1, 1988, abandoned.

[51] Int. Cl.$^5$ .................... C07H 21/00; C12Q 1/68
[52] U.S. Cl. ........................................... 536/27; 435/6; 435/91; 436/501; 935/16; 935/78; 935/86; 935/88
[58] Field of Search ............... 435/6, 91; 436/501; 536/27; 935/19, 78, 86, 88

[56] References Cited

U.S. PATENT DOCUMENTS

| 4,086,417 | 4/1978 | Ishida et al. ............... 536/29 |
| 4,088,639 | 5/1978 | Zapelli et al. .............. 260/112.5 R |
| 4,213,893 | 7/1980 | Carrico et al. ............. 260/112.5 R |
| 4,228,237 | 10/1980 | Hevey et al. ............... 435/7 |
| 4,230,698 | 10/1980 | Bobek et al. ............... 424/180 |
| 4,267,171 | 5/1981 | Bergstrom et al. .......... 424/180 |
| 4,687,732 | 8/1987 | Ward et al. ................ 435/6 |
| 4,711,955 | 12/1987 | Ward et al. ................ 536/29 |
| 4,737,454 | 4/1988 | Dattagupta et al. ......... 435/6 |
| 4,910,300 | 3/1990 | Urdea et al. ............... 536/287 |

FOREIGN PATENT DOCUMENTS

| 70685 | 1/1983 | European Pat. Off. . |
| 70686 | 1/1983 | European Pat. Off. . |
| 70687 | 1/1983 | European Pat. Off. . |
| 97373 | 1/1984 | European Pat. Off. . |
| 254051 | 1/1988 | European Pat. Off. . |
| 258017 | 3/1988 | European Pat. Off. . |
| WO83/02276 | 7/1983 | PCT Int'l Appl. . |
| WO83/02277 | 7/1983 | PCT Int'l Appl. . |
| WO83/02286 | 7/1983 | PCT Int'l Appl. . |
| WO88/00695 | 1/1988 | PCT Int'l Appl. . |
| WO89/06701 | 7/1989 | PCT Int'l Appl. . |
| 2019408 | 10/1979 | United Kingdom . |
| 2125964 | 3/1984 | United Kingdom . |

OTHER PUBLICATIONS

J. G. L. Bauman et al., "A New Method For Fluorescent Miscroscopical Localization Of Specific DNA Sequences by In Situ Hybridization of Fluorochrome-Labeled RNA", *Exp. Cell Res.*, 128, pp. 485-490 (1980).

J. G. J. Bauman et al, "Rapid And High Resolution Detection Of An In situ Hybridization To Polytene Chromosomes Using Fluorochrome-Labeled RNA", *Chromosoma* (Berl.), 84, pp. 1-18 (1981).

E. A. Bayer and M. Wilchek, "The Use Of The Avidin-Biotin Complex As A Tool In Molecular Biology", in *Methods of Biochemical Analysis*, 26, pp. 1-45 (1980).

T. R. Broker et al., "Electron Microscopic Visualization of tRNA Genes With Ferritin-Avidin: Biotin Label", *Nucl. Acids Res.*, 5, pp. 363-383 (1978).

I. Bronstein et al., "A Comparison Of Chemiluminescent And Colorimetric Substrates In A Heptitis B Virus DNA Hybridization Assay", (submitted to *Nucl. Acids Res.*, Oct. 1988).

B. C. F. Chu et al., "Synthesis Of Amplifiable Reporter For Bioassays", *Nucl. Acids Res.*, 14, pp. 5591-5603 (1986).

(List continued on next page.)

*Primary Examiner*—Robert A. Wax
*Assistant Examiner*—Ardin H. Marschel
*Attorney, Agent, or Firm*—Leon R. Yankwich; James F. Haley, Jr.

[57] ABSTRACT

A polynucleotide probe with a label bearing a plurality of signalling moieties. The label is attached to the probe by the reaction of an amino and sulfhydryl reactive hetero bifunctional reagent with the probe and label, the reaction resulting in the oxidation of a sulfhydryl group of the label. The label may be attached to the 5' terminus of the probe, or to modified bases of the probe. Probes constructed according to the invention are useful in detecting target sequences in genomic DNA.

7 Claims, 2 Drawing Sheets

OTHER PUBLICATIONS

B. C. F. Chu and L. E. Orgel, "Ligation Of Nucleotides To Nucleic Acids Or Proteins Via Disulfide Bonds", *Nucl. Acids Res.*, 16, pp. 3671–3691 (1988).

B. J. Conner et al., "Detection Of Sickle Cell-Globin Allele By Hybridization With Synthetic Oligonucleotides", *Proc. Nat. Acad. Sci. U.S.A.* 80, pp. 278–282 (1982).

A. F. Cook et al., "Synthesis And Hybridization Of A Series Of Biotinylated Oligonucleotides", *Nucl. Acids Res.*, 16, pp. 4077–4095 (1988).

P. E. Devlin et al., "Southern Analysis Of Genomic DNA With Unique And Degenerate Oligonucleotide Probes: A Method For Reducing Probe Degeneracy", *DNA* 7, pp. 449–507 (1988).

A. C. Forster et al., "Non-Radioactive Hybridization Probes Prepared By The Chemical Labeling Of DNA And RNA With A Novel Reagent, Photobiotin", *Nucl. Acids Res.*, 13, pp. 745–754 (1985).

G. J. Garbut et al., "Use Of Biotinylated Probes For Detecting Sickle Cell Anemia", *Clinical Chemistry*, 31, pp. 1203–1206 (1985).

M. Grunstein and D. S. Hogness "Colony Hybridization: A Method For The Isolation Of Cloned DNAs That Contain A Specific Gene", *Proc. Nat. Acad. Sci. U.S.A.*, 72, pp. 3961–3965 (1975).

J. Haralambidis et al., "The Solid Phase Synthesis Of Oligonucleotides Containing A 3' Peptide Moiety", *Tetrahedron Letts.*, 28, pp. 5199–5202 (1987).

H. Heitzmann et al., "Use Of The Avidin Biotin Complex For Specific Staining Of Biologic Membranes In Electron Microscopy", *Proc. Nat. Acad. Sci. U.S.A.*, 71, 3537–3541 (1974).

K. Hoffman et al., "Characterization Of The Functional Groups Of Biotin", *J. Biol. Chem.*, 141, pp. 207–211 (1941).

E. Jablonski et al., "Preparation Of Oligonucleotide-Alkaline Phosphatase Conjugates And Their Use As Hybridization Probes", *Nucl. Acids Res.*, 14, pp. 6115–6127 (1986).

D. T. Kingsbury, "DNA Probes In The Diagnosis Of Genetic And Infectious Diseases", *Trends In Biotech.*, 5, pp. 107–111 (1987).

P. R. Langer et al., "Enzymatic Synthesis Of Biotin-Labeled Polynucleoties: Novel Nucleic Acid Affinity Probes", *Proc. Nat. Acad. Sci. U.S.A.* 78, pp. 6633–6637 (1981).

P. R. Langer and D. C. Ward, "A Rapid And Sensitive Immunological Method For In-situ Gene Mapping", in *Developmental Biology Using Purified Genes*, ed. D. D. Brown, Academic Press, pp. 647–658 (1981).

I. R. Lehman and E. A. Pratt, "On the Structure Of The Glucosylated Hydroxymethylcytosine Nucleotides Of Coliphages T2, T4 and T6", J. Biol. Chem., 235, pp. 3254–3259 (1960).

J. J. Leary et al., "Rapid And Sensitive Colorimetric Method For Visualizing Biotin-Labeled DNA Probes Hybridized To DNA or RNA Immobilized On Nitrocellulose: Bio-Blots", *Proc. Nat. Acad. Sci. U.S.A.*, 80, pp. 4045–4049 (1983).

M. Lemaitre et al., "Specific Antiviral Activity Of A Poly(L-lysine)-Conjugated Oligodeoxyribonucleotide Sequence Complementary To Vesicular Stomatitis Virus N Protein mRNA Initiation Site", *Proc. Nat. Acad. Sci. U.S.A.*, 84, pp. 648–652 (1987).

P. Li et al., "Enzyme-Linked Synthetic Oligonucleotide Probes: Non-Radioactive Detection of Enterotoxigenic *Escherichia coli* in Faecal Specimens", *Nucl. Acids Res.*, 15, pp. 5275–5287 (1987).

M. Litt, "Structural Studies On Transfer Ribonucleic Acid. I. Labeling Of Exposed Guanine Sites In Yeast Phenylalanine Transfer Ribonucleic Acid With Kethoxal", *Biochemistry*, 8, pp. 3249–3253 (1969).

J. Manning et al., "A Method for Gene Enrichment Based on the Avidin-Biotin Interaction. Application To The Drosophila Ribosomal RNA Gene", *Biochemistry*, 16, pp. 1364–1370 (1977).

J. E. Manning et al., "A New Method Of In situ Hybridization", *Chromosoma* (Berl.), 53, pp. 107–117 (1975).

S. Nishimura et al., "Synthetic Nucleosides And Nucleotides: XV. 5—Dimethylamino—2—Ooxidiosoquinolin—1—yl Diazomethane: A Novel Water Soluble Fluorescent Labelling Agent for Nucleotides", *Chem. Pharm. Bull.*, 28(6): 1965–1703 (1980).

M. Pellegrini et al., "Application Of The Avidin-Biotin Method of Gene Enrichment To The Isolation Of Long Double-Stranded DNA Containing Specific Gene Sequences", *Nucl. Acids Res.*, 4, 2961–2973 (1977).

S. M. Politz et al., "Ribonucleic Acid-Protein Cross-Linking In *Escherichia coli* Ribosomes: (4-Azidophenyl)glyoxal, A Novel Heterobifunctional Reagent", *Biochemistry*, 20, pp. 372–378 (1981).

J. Reiser et al., "Transfer of Small DNA Fragments (List continued on next page.)

OTHER PUBLICATIONS

From Polyacrylamide Gels to Diazobenzyloxymethyl Paper And Detection By Hybridization With DNA Probes", *Biochem. and Biophys. Res. Comm.*, 85, pp. 1104–1112 (1978).

M. Renz and C. Kurz, "A Colorimetric Method For DNA Hybridization", *Nucl. Acids Res.*, 12, pp. 3435–3444 (1984).

P. W. J. Rigby et al., "Labeling Deoxyribonucleic Acid To High Specific Activity In Vitro by Nick Translation With DNA Polymerase I", *J. Mol. Bio.*, 113 pp. 237–251 (1977).

R. Shapiro and J. Hachman, "The Reaction Of Guanine Derivatives With 1,2 Dicarbonyl Compounds", *Biochemistry*, 5, pp. 2799–2807 (1966).

R. H. Singer and D. C. Ward, "Actin Gene Expression Visualized in Chicken Muscle Tissue Culture By Using In Situ Hybridization With A Biotinated Nucleotide Analog", *Proc. Nat. Acad. Sci. U.S.A.*, 79, 7331–7335 (1982).

H. A. Staab, "New Methods Of Preparative Organic Chemistry IV. Syntheses Using Heterocyclic Amides (Azolides)", *Angew. Chem. Internat. Ed.*, 1, pp. 351–367 (1962).

J. Stavrianopoulos et al., "Glycosylated DNA Probes For Hybridization/Detection of Homologous Sequences", *DNA*, 2, p. 73 (1983) (abstr.).

M. S. Urdea et al., "A Novel Method For The Rapid Detection Of Specific Nucleotide Sequences In Crude Biological Samples Without Blotting Or Radioactivity; Application To The Analysis Of Hepatitis B Virus In Human Serum", *Gene*, 61, pp. 253–264 (1987).

L. Wachter et al. "A Simple And Efficient Procedure For The Synthesis of 5'-aminoalkyl Oligonucleotides", *Nucleic Acids Res.*, 14, pp. 7985–7993 (1986).

"Antisense Molecular Biology and 'S—Oligos'", *Synthesis*, 1, (1988).

NUCLEIC ACID PROBE LINKED TO A LABEL HAVING A TERMINAL CYSTEINE

This is a continuation-in-part of application Ser. No. 200,930, filed Jun. 1, 1988, now abandoned.

TECHNICAL FIELD OF THE INVENTION

This invention relates to polynucleotide probes for detecting target nucleic acid sequences in an analyte. More particularly, this invention relates to labeled polynucleotide probes in which a polypeptide or other organic molecule serves to label the probe and to make it detectable. As will be appreciated, the labeled probes of this invention are useful in many laboratory, industrial and medical applications wherein detection of a target base sequence in a nucleic acid is desired.

BACKGROUND OF THE INVENTION

In this description, the following terms are employed:

Analyte - A substance or substances, either alone or in admixtures, whose presence is to be detected and, if desired, quantitated. The analyte may be a DNA or RNA molecule of small or high molecular weight, a molecular complex including those molecules, or a biological system containing nucleic acids, such as a virus, a cell, or a group of cells. Among the common analytes are nucleic acids (DNA and RNA) or segments thereof, either single- or double-stranded, viruses, bacteria, cells in culture, and the like. Also included are fungi, algae, other microorganisms, as well as animals (e.g., vertebrates) and plants, their cells, tissues and fluids.

Bridging Moiety - That moiety which on covalent attachment or non-covalent binding to the label of a polynucleotide sequence acts as a connection between the label and a signalling moiety.

Genomic DNA - An analyte comprising the DNA of an organism. Typically, the analyte will be purified nuclear DNA, and may, although not necessarily, include all nucleotide sequences present in the organism's DNA.

Label - That moiety attached to the probe by a linkage group which as is, or which after covalent attachment of a signalling moiety or a combination of bridging moiety and signalling moiety to it, or which after non-covalent binding of a signalling moiety or a combination of bridging moiety and signalling moiety to it, gives rise to a signal which is detectable, and in some cases, quantifiable.

Linkage Group - That moiety which serves to link or attach a label to the probe. The linkage group serves to hold the label away from the probe, so as to prevent interference with binding between the probe and target.

Probe - A polynucleotide sequence which is complementary to a target polynucleotide sequence in the analyte.

Signal - That characteristic of a label or signalling moiety that permits it to be detected.

Signalling Moiety - That moiety which on covalent attachment or non-covalent binding to the probe, label or to a bridging moiety attached or bound to the probe or label provides a signal for detection of the label and the moiety to which the label is attached.

Target - The specific sequence of bases in a nucleic acid present in an analyte whose presence is to be detected.

The analysis and detection of minute quantities of substances in biological and non-biological samples has become a routine practice in clinical and analytical laboratories. These detection techniques can be divided into two major classes: (1) those based on ligand-receptor interactions (e.g., immunoassay-based techniques) and (2) those based on nucleic acid hybridization (polynucleotide sequence-based techniques).

Immunoassay-based techniques are characterized by a sequence of steps comprising the non-covalent binding of an antibody and an antigen complementary to it. See, for example, T. Chard, *An Introduction To Radioimmunoassay And Related Techniques* (1978).

Polynucleotide sequence-based detection techniques are characterized by a sequence of steps comprising the non-covalent binding of a labelled polynucleotide sequence or probe to a complementary sequence of the analyte under conditions which permit hybridization of the bases through Watson-Crick pairing, and the detection of that hybridization. [M. Grundstein and D. S. Hogness, "Colony Hybridization: A Method For The Isolation Of Cloned DNAs That Contain A Specific Gene", *Proc. Nat. Acad. Sci. USA*, 72, pp. 3961–65 (1975); D. T. Kingsbury, "DNA Probes In The Diagnosis Of Genetic And Infectious Diseases", Trends In Biotechnology, 5, pp. 107–11 (1987).]

The non-covalent binding of a labelled sequence or probe to a complementary sequence of an analyte is the primary recognition event of polynucleotide sequence-based detection techniques. This binding event is brought about by a precise molecular alignment and interaction of complementary nucleotides of the probe and target. It is energetically favored by the release of non-covalent bonding free energy, e.g., hydrogen bonding, stacking free energy and the like.

In order to employ the non-covalent binding of a probe for the determination of an analyte containing a target sequence, it is necessary to be able to detect binding of the probe to the target. This detection is effected through a signalling step or event. A signalling step or event allows detection in some quantitative or qualitative manner of the occurrence of the primary recognition event.

In general, the use of a separate label moiety to attach a signal moiety to a probe is a desirable way to couple the primary recognition and signal events. First, this technique permits attachment of large bridging and signalling moieties to the probe, while interfering only minimally with the structure of the probe, and therefore with its binding to the target. Second, use of a separate label permits the indirect attachment of many signalling moieties to a single locus within a probe molecule. Attachment of a label bearing many signalling moieties at a single point, rather than attaching signalling moieties to many bases, serves to minimize the likelihood that binding between the probe and target will be disturbed, while providing a larger signal than with a single signalling moiety. An additional improvement is to employ a linkage group as a rigid point of attachment between the label and probe, which will hold the label away from the probe during hybridization.

The primary recognition event and the signalling event of polynucleotide sequence based detection techniques may be coupled either directly, proportionately or inverse proportionately. Thus, in such systems as nucleic acid hybridization assays performed with detectable probes, the amount of signal is usually directly proportional to the amount of analyte present. Inversely proportional techniques include, for example, competitive assays, wherein the amount of detected signal decreases with increasing amounts of analyte present in the sample.

Amplification techniques are of great importance when only a small amount of a target is present. For example, the signalling component of the assay may be present in a ratio of 10:1 for each recognition component, thereby providing a 10-fold increase in sensitivity.

A wide variety of signalling events may be employed to detect the occurrence of the primary recognition event. The signalling event chosen depends on the particular signal that characterizes signalling moiety employed. Although the label itself, without further treatment, may be detectable, more often, either the signalling moiety is attached covalently, or bound non-covalently to a label or a combination of signalling and bridging moieties in order to render the primary recognition event detectable.

Although the combination of bridging moiety and signalling moiety, described above, may be constructed before attachment or binding to the label, it may also be sequentially attached or bound to the label. For example, the bridging moiety may be first bound or attached to the label and then the signalling moiety combined with the joined label and bridging moiety. In addition, it should be understood that several bridging moieties and/or signalling moieties may be employed together in any one combination of bridging moiety and signalling moiety.

Examples of the covalent attachment of a signalling moiety or a combination of bridging moiety and signalling moiety to a label include chemical modification of the label with signalling moieties. In addition, the primary recognition event may be detected by the non-covalent binding of a signalling moiety or a combination of bridging moiety and signalling moiety that itself can be detected by appropriate means, or the non-covalent binding to the label of a combination of bridging moiety and signalling moiety to provide a signal that may be detected by one of those means. For example, the label could be bound to a bridging moiety, e.g., a lectin, and then bound through the lectin, or bridging moiety, to another moiety that is detectable by appropriate means.

There are a wide variety of signalling moieties and bridging moieties that may be employed for covalent attachment or non-covalent binding to the label of polynucleotide sequences useful as probes in analyte detection systems. All that is required is that the signalling moiety provide a signal that may be detected by appropriate means and that the bridging moiety, if any, be characterized by the ability to attach covalently or to bind non-covalently to the label, and also possess the ability to combine with a signalling moiety.

Signalling moieties may be radioactive or non-radioactive. Radioactive signalling moieties are characterized by one or more radioisotopes of phosphorous, iodine, hydrogen, carbon, cobalt, nickel, and the like. Preferably the radioisotope emits $\beta$ or $\gamma$ radiation, and has a long half life. Detection of radioactive signalling moieties is typically accomplished by the stimulation of photon emission from crystalline detectors caused by the radiation, or by the fogging of a photographic emulsion.

Non-radioactive signalling moieties have the advantage that their use does not pose the hazards associated with exposure to radiation, and that special disposal techniques after use are not required. [D. T. Kingsbury, (1987), p. 108.] In addition, they are generally more stable, and as a consequence, cheaper to use. Detection sensitivities of non-radioactive signalling moieties may be as high or higher than those of radioactive signalling moieties.

Among the preferred non-radioactive signalling moieties or combinations of bridging and signalling moieties useful with non-radioactive labels are those based on the biotin/avidin binding system [P.R. Langer et al., "Enzymatic Synthesis of Biotin Labeled Polynucleotides: Novel Nucleic Acid Affinity Probes", *Proc. Nat. Acad. Sci. USA*, 78, pp. 6633-37 (1981). R. H. Singer and D. C. Ward, "Actin Gene Expression Visualized In Chicken Muscle Tissue Culture By Using In Situ Hybridization With A Biotinated Nucleotide Analog", *Proc. Nat. Acad. Sci USA*, 79, pp. 7331-35 (1982)]. For a review of non-radioactive signalling and bridging-signalling systems, see U.S. Pat. No. 4,711,955.

Non-radioactively labeled polynucleotides are not more widely used in detection systems because the attachment of a label which does not interfere with hybridization is expensive and because of difficulties in attaching the signalling moiety to the probe. The chemical reaction conditions that might be useful for modification of a polynucleotide to add it to a label are often too vigorous to be sufficiently selective for a particular nucleotide. More importantly, chemical labelling of polynucleotide sequences often interferes with the hydrogen bonding necessary for hybridization. For example, dicarbonyl reagents, such as glyoxal and kethoxal, react with guanine residues, but the glyoxal and kethoxal reacted nucleotides do not hybridize to complementary sequences in the analyte because the glyoxal or kethoxal moiety interferes with the hydrogen bonding necessary for hybridization [M. Litt, "Structural Studies on Transfer Ribonucleic Acid. I. Labeling Of Exposed Guanine Sites in Yeast Phenylalanine Transfer Ribonucleic Acid with Kethoxal", *Biochemistry*, 8, pp. 3249-53 (1969)].

An alternative approach, such as that disclosed in U.S. Pat. No. 4,711,955, provides for covalent attachment of a label to individual bases by way of a linkage group. Labeled probes must then be constructed from labeled and unlabeled bases using a polynucleotide complementary to the probe as a template. Thus little specificity as to the location of the label on the probe is possible, and as consequence, steric interference between adjacent labels is possible. In addition, synthesis of the labeled monomeric nucleotides prior to incorporation into the polynucleotides involves expensive chemical processes. The coupling of the labelled monomeric nucleotides into a polynucleotide is also expensive, as the cost of the enzymes used in enzymatic coupling is substantial.

A further deficiency of a labeling technique in which individual nucleotides of a probe sequence are labeled is that the signal intensity is generally low. Because a single signalling moiety is attached to each nucleotide base, in order to achieve a level of signal intensity that is readily detectable, a long probe molecule is required. This reduces the ability of the probe to detect minor mismatches between the probe and analyte, since sufficient hydrogen bonding between other bases will cause the probe to remain bound to the analyte during washing. Detection of single mismatches between base pairs is of critical importance in diagnosing certain inherited diseases such as sickle-cell anemia [B. J. Conner et al., "Detection of Sickle Cell $\beta^s$-Globin Allele By Hybridization With Synthetic Oligonucleotides, *Proc. Nat. Acad. Sci. USA*, 80, pp. 278-82 (1983)].

A particularly important application of the present invention is in screening an organism's entire genome in order to detect a particular target base sequence. For example, it is desirable to detect the presence of inheritable diseases in potential human parents in cases where the disease does not manifest itself until after child bearing age has been attained, as in Huntington's chorea, and in diseases where heterozygous individuals are merely carriers, as in sickle cell anemia and Tay Sachs disease. Genomic screening requires a probe having great sensitivity. Moreover, effective genomic screening requires a short probe capable of detecting a mutation at a single base within the affected gene in order to detect inheritable diseases resulting from alteration at only a single base, such as sickle cell anemia Conner et al., 1983]. A probe capable of selectively detecting a target polynucleotide sequence in an analyte of genomic DNA or RNA may be termed a genomic probe. To date no genomic probes apart from those bearing radioactive signalling moieties and those greater than about 400 base pairs in length have been disclosed which are capable of distinguishing mutant from wild type individuals. As will be demonstrated below, short probes prepared according to the present invention are capable of doing so.

SUMMARY OF THE INVENTION

The present invention solves both the problems associated with use of radiolabeled probes and with prior art methods of probe labeling by providing a polynucleotide probe and a label bearing a plurality of signalling moieties. The label is attached to the probe by the reaction of an amino and sulfhydryl reactive hetero bifunctional reagent with the probe and label, the reaction resulting in the oxidation of a sulfhydryl group of the label. The mode of attachment between the probe and label serves to reduce interference during hyb.ridization between the probe and target polynucleotides. In one embodiment the point of attachment is an amino group at the 5' terminus of the probe. In an alternative embodiment, the point of attachment is an amine group affixed to a modified base within the probe. The present invention provides for amplification of the signal resulting from probe binding by permitting attachment of a plurality of signalling moieties to the label. Another aspect of the invention provides a method for detection of alterations in the sequence of nucleotides in genomic DNA. The method employs the labeled nucleic acid probes of this invention, and is sensitive enough to detect alterations of a single nucleotide within a gene.

DETAILED DESCRIPTION OF THE INVENTION

Figure 1:
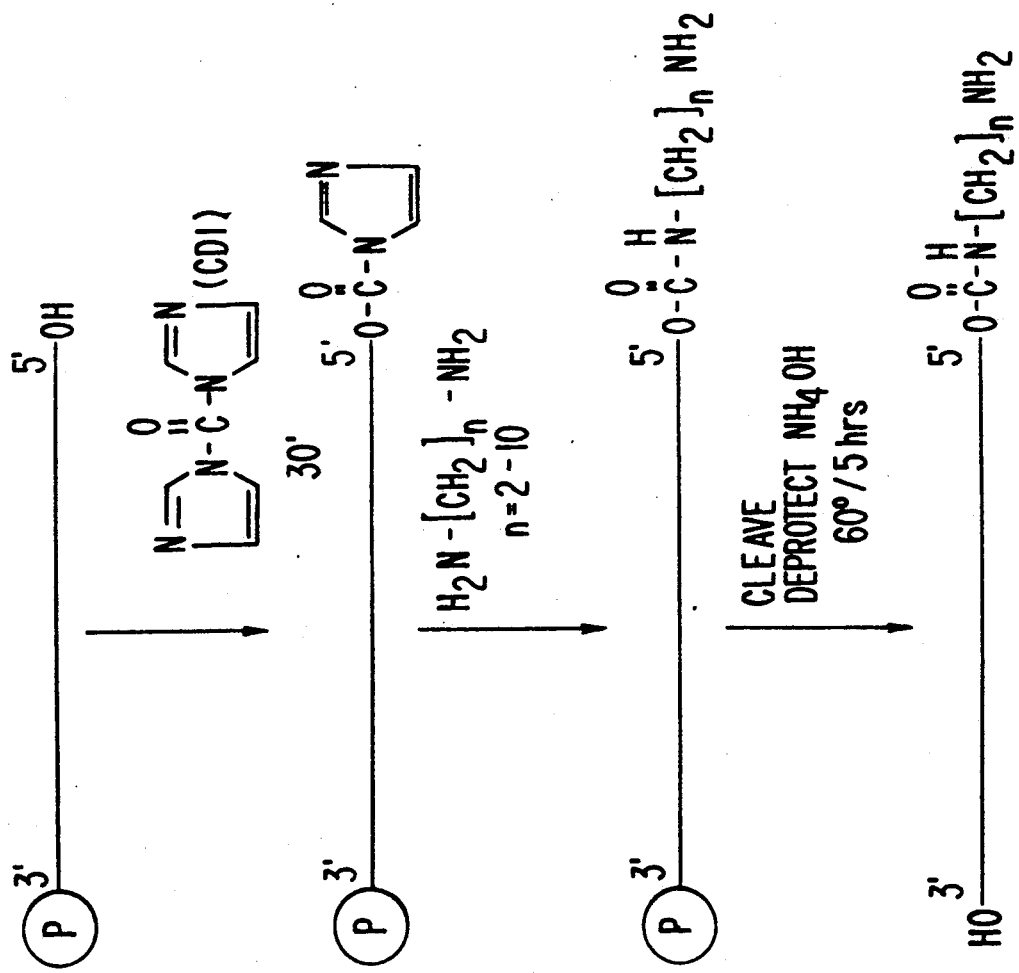
FIG. 1 is a schematic outline of the chemical reactions employed in activating the 5' —OH group of the polynucleotide probe.
Figure 2:
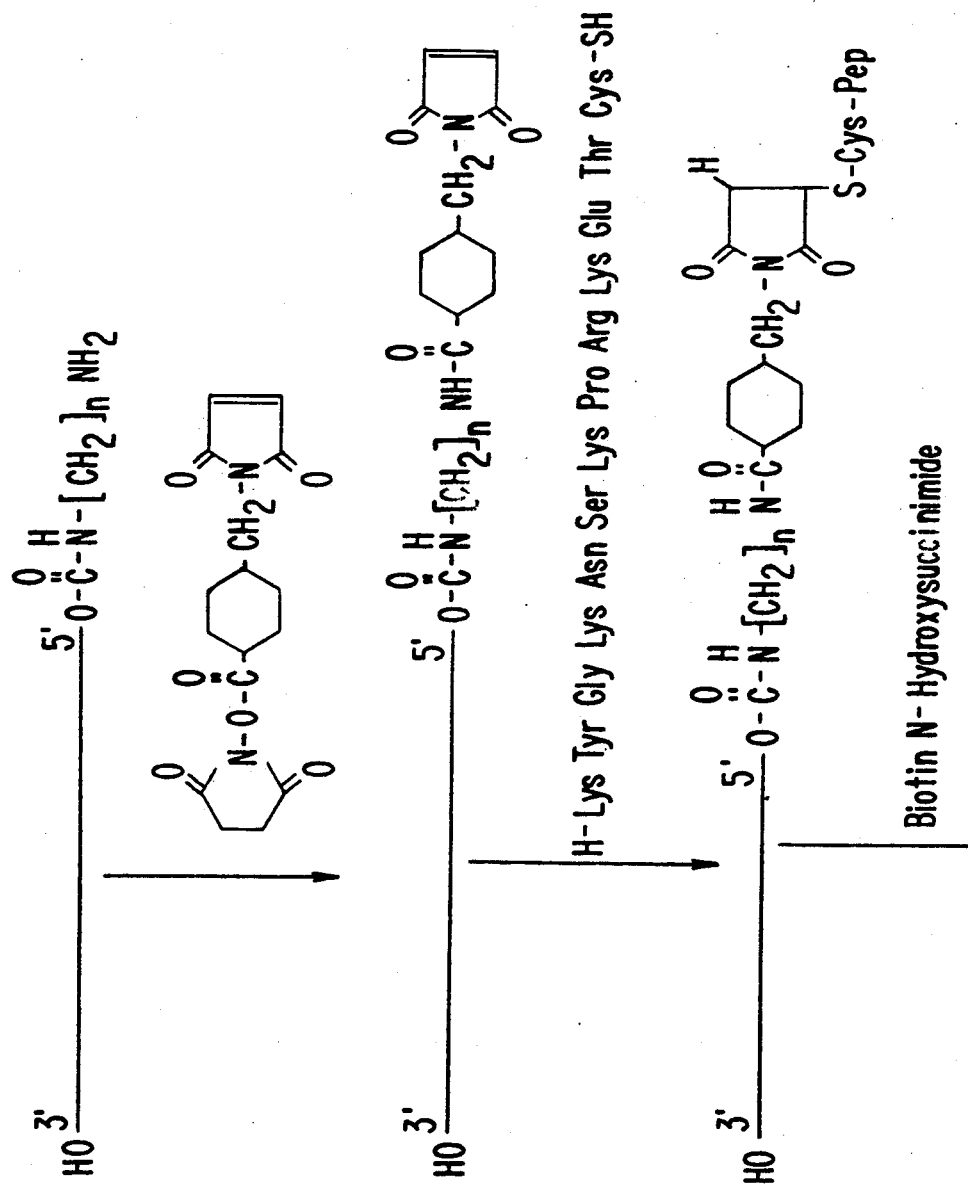
FIG. 2 is a schematic outline of the chemical reactions employed in attaching the label to the activated polynucleotide probe.

According to the present invention, a nucleic acid probe molecule with a nucleotide sequence complementary to that of a target sequence in the analyte is labeled by covalently attaching an organic molecule comprising a reactive sulfhydryl group to the 5' terminus of the probe. In a preferred embodiment, the label is a polypeptide strand with a cysteine residue at its amino terminus. Alternatively, the label may be any molecule with reactive amino groups and at least one sulfhydryl group. The polypeptide strand includes, preferably, a plurality of residues bearing reactive carboxyl and/or amino groups. As examples, lysine and ornithine possess reactive amino groups, while aspartic acid and glutamic acid possess reactive carboxyl groups. In the preferred embodiment, bridging moieties are attached to the polypeptide after the polypeptide is attached to the probe. Preferred bridging moieties include biotin and iminobiotin. After the labeled probe has hybridized to an analyte, these labels may be detected by exposing them to a signal moiety, or to a second bridging moiety with a signalling moiety attached thereto. Preferably avidin or streptavidin are the second bridging moieties to which a signal moiety has been attached.

In an alternative embodiment, instead of covalent attachment of biotin to residues bearing reactive amino groups, radioactive iodine atoms may be covalently attached to tyrosine residues in the polypeptide strand. In yet another embodiment, coumarin may be attached to residues bearing reactive carboxyl groups. The presence of coumarin may be detected optically or by immunochemical means. As will be plain, other combinations of label and signal may be employed.

Any of a large number of nucleic acid sequences may be employed in accord with this invention for use as probes in the detection of analytes. Included, for example, are target sequences in both RNA and DNA, as are the polynucleotide sequences that characterize various viral, viroid, fungal, parasitic or bacterial infections, genetic disorders or other sequences in analytes that it is desired to detect. Probes may be of synthetic, semi-synthetic or natural origin. Probe molecules include both polyribonucleotides and polydeoxynucleotides.

Although the presently preferred embodiment employs probes of approximately 30 base pairs, shorter probes may be used, provided they are capable of specifically and stably hybridizing to the target sequence. The probe may be designed to hybridize to either the sense or antisense strand of a DNA duplex. When the target is messenger RNA, however, the sequence of the probe should be complementary to it. The guanine and cytosine content of the probe is not critical for its ability to detect target sequences.

Synthesis of the labeled probe according to this invention is carried out in a series of steps. In the preferred embodiment, the probe molecule is activated at its 5' terminus by aminoalkylation. This may be achieved through the modification of the 5' —OH group as its 5'-imidazoyl derivative using carbonyldiimidazole, which is subsequently displaced by an aminoalkyl compound such as hexamethylenediamine. A detailed description of a procedure for practicing this embodiment may be found in Wachter et al., "A Simple And Efficient Procedure For The Synthesis Of 5'-Aminoalkyl Oligodeoxynucleotides", *Nucleic Acids Research*, 14, pp. 7985-94 (1986). Other diamines can be used in place of the hexamethylenediamine of the preferred embodiment. Alternatively, the 5'—OH may be activated by other azolides [H. A. Staab, "Synthesis Using Heterocyclic Amides [Azolides]", *Angew. Chemie International Edition*, 1, pp. 351-67 (1962], or with mestiylenesulfonyl or para-toluenesulfonyl groups, followed by amination by an $SN_2$ displacement reaction.

The label may be of any reasonable length. In order to permit covalent attachment of the linkage group and the label, the label preferably includes a reactive sulfhydryl group. Preferably, the label also includes reactive groups to which the bridging moiety or signal moiety may be attached. The label may be any organic molecule with the foregoing attributes. In the preferred embodiment, the label is a polypeptide and the bridging moieties are attached to the amino groups of ornithine or lysine residues and the carboxyl groups of aspartic acid and glutamic acid residues. Preferably, the polypeptide label has at least five bridging moieties attached to it. Alternatively, signalling moieties may be attached directly to these residues.

When the label is a polypeptide, the polypeptide strand may be synthesized chemically, relying on well known techniques. Alternatively, it may be derived from natural sources.

In order to minimize interference between bridging moieties and/or signalling moieties attached to a polypeptide strand, the residues to which the bridging or signalling moieties are attached should not be adjacent. Such spacing also facilitates access to the bridging moieties or reactive residues by second bridging moieties and signal moieties.

When the label is a polypeptide, the polypeptide strand includes a cysteine residue or other modified residue bearing a sulfhydryl group. In the preferred embodiment, the sulfhydryl group occurs at the amino or carboxyl terminus of the polypeptide strand. By this arrangement, the probe and label are non-adjacent, since the label is attached at the 5' terminus of the probe.

When the label comprises amino acid residues, the residues may be chosen from among those which are hydrophilic, such as glycine, asparagine, aspartic acid, glutamic acid, serine, threonine, histidine, arginine and tyrosine. One can also form a label which includes any of the natural amino acids or their D isomers provided that charge or steric hindrance between residues and between residues and bridging moieties, if present, do not interfere with access to the label by signalling moieties or second bridging moieties such as avidin or streptavidin.

Preferably, the label is attached to the activated probe by way of a linkage group formed by sequentially reacting an amino and sulfhydryl reactive, hetero bifunctional group with the activated probe and then with the label. Preferably, the linkage is formed by reacting the activated probe molecule with succinimidyl 4-[N-maleimidomethyl] cyclohexane-1-carboxylate resulting in release of N-hydroxy succinimide in the nucleophilic substitution reaction, followed by exposure of the derivatized probe to a label molecule bearing a reactive sulfydryl group. Other compounds, such as metamaleimidobenzoyl-N-hydrosuccinimide ester, N-succinimidyl 4-iodoacetyl] aminobenzoate, N-succinimidyl [4-bromoacetyl] and N-succinimidyl 3-[2-pyridylthio] propionate may be used to form a linkage group. The resulting label is held away from the probe by the linkage thus formed.

A useful feature of the labeled probes of this invention is that multiple signal moieties may be attached to each probe. Thus amplification of each primary recognition event is provided. In the preferred embodiment bridging moieties are attached to five lysine residues in the labeled polypeptide strand. Assuming that the signal produced is proportional to the number of label molecules present, this technique provides at least a five fold amplification of the signal. Further amplification is possible if a second bridging moiety, or combination of bridging moieties bearing multiple signalling moieties, is employed.

Depending upon the label used, the signalling moiety may be chosen to bind directly to the label. Preferably, however, the signal is attached to a bridging moiety, and the bridging moiety binds to the label. For example, when biotin is used as a bridging moiety, avidin may be used as a second bridging moiety, and the avidin may have attached to it a fluorescein molecule as signalling moiety. Alternatively, a bridging moiety may be an antibody to the label. Yet another alternative within the scope of this invention would be to employ a first antibody as a bridging moiety, and a second antibody, bearing a signalling moiety, as a second bridging moiety.

In the preferred embodiment, biotin is used as a bridging moiety. Biotin is attached to the probe by incubating the labeled probe with biotin N-hydroxysuccinimide. This results in the covalent bonding of biotin molecules to the reactive amino groups present in the probe.

A modified version of this procedure may also be employed to label base moieties of nucleotides. Rather than attaching the linkage group of the present invention to a 5' —OH derivatized probe, the same linkage group may be used to attach a label to the reactive amino function of the modified base of Langer et al. (1981), and Ward et al., U.S. Pat. 4,711,955, without significant changes in chemistry. In particular, since the linkage groups of the modified bases disclosed in the above documents bear reactive amine functions, they also will react with an amino and sulfhydryl reactive hetero bifunctional reagent, permitting attachment of a label thereto. When bases are labeled in this way, two linkage groups connect the label to the probe. The linkage group attached to the base by the method of Langer et al. may be termed a first linkage group, and the linkage group formed by reaction between the amine function of the modified base, and the amino and sulfhydryl reactive hetero bifunctional reagent and the label as a second linkage group. Bridging and signalling moieties may be attached to the labeled probe as previously described.

EXAMPLES

In order that this invention may be better understood, the following examples are set forth. These examples are for purposes of illustration only, and are not to be construed as limiting the scope of the invention in any manner.

EXAMPLE 1

Preparation and Activation of a DNA Probe a) Probe Synthesis

Four DNA probes were prepared using an Applied Biosystems Model 380A automated DNA synthesizer. The base sequences of the probes were:

1. 5' GAC CAC GCT GCT CTC CTG GGC ACA GCG GGA CGA ATC CGA 2. 5' CAC GCT GCT CTC CTG GGC ACA GCG GGA CGA 3. 5' TTG CTG GTA TAT CAT CTG CGT TTT TTC ATG 4. 5' TTG CTG GTA TAT CAC CTG CGT TTT TTC ATG

The synthesizer was programmed for DMTr[a]-off, using a manual ending method. The monomers used for constructing the probe were fully protected nucleoside-O-methylphosphoramidite monomers.

[a]Dimethoxytrityl group.

All of the above probes were anti-sense (complementary) to the gene coding for human tissue plasminogen activator ("tPA"). Probe 2 was a shorter version of probe 1. Probe 3 and probes 1 and 2 were complementary to different regions of the tPA gene. Probe 4 was the same as probe 3 except at the underlined position, which was an intentionally introduced mismatch.

b) Aminoalkylation Of Probes

The 5' —OH group of the probe was activated as its 5' aminoalkyl derivative using a modified version of the method described by Wachter et al., 1986. During and after synthesis, the probes were attached to a solid support of aminopropyl controlled pore glass beads (Electronucleonics). After synthesis of the probe, the solid support, with the probe still attached to it, was taken up in a small reaction vessel having a medium porosity frit and a stop-cock. The probe was washed well under anhydrous conditions with dry acetonitrile. Carbonyldiimidazole (50 mg) was dissolved in 1 ml of anhydrous acetonitrile and this solution was introduced into the reaction vessel. The activation reaction was allowed to proceed for 30 minutes at room temperature with occasional shaking. After this time, the solid support was washed well with dry acetonitrile.

The 5'-aminoalkyl derivative of the probe was prepared by reacting the activated probe with a 1 ml solution of 0.3 M hexamethylenediamine dissolved in isopropanol. The nucleophilic substitution reaction was allowed to proceed for one hour at room temperature with occasional shaking. At the end of one hour, the reagents were washed off with isopropanol followed by methanol. The probe, while still attached to the solid support, was air dried.

After drying, the probe was treated with a 1 ml solution of thiophenol:triethylamine: dioxane (1:2:2) for 30 minutes to remove the phosphate protecting groups. The oligomer was cleaved from the solid support with concentrated ammonium hydroxide for one hour. The reaction mixture was then warmed to about 55° C. for about 5 hours to remove the base protecting groups. The ammonium hydroxide was removed by drying the reaction mixture under vacuum.

After evaporation of the ammonium hydroxide, the activated probe was taken up in water and lyophilized. Initial purification, based on size, was performed using a 5 ml SEPHADEX ™ gel filtration media G25 column (Pharmacia) equilibrated with 50 mM triethylammonium acetate at pH 7.0. Six 10 drop fractions were collected and the fraction containing the probe molecule was purified using either gel electrophoresis or high performance liquid chromatography ("HPLC").

When HPLC purification was employed, solvent A consisted of a mixture of 10% acetonitrile and 90% 50 mM triethylammonium acetate ("TEAA") at pH 7.0, and solvent B was a mixture of 80% actetonitrile and 20% TEAA, also at pH 7.0. The solvents were applied to a $C_8$ column (Biorad) so as to create a gradient of 0% solvent B initially, increasing to 25% solvent B at 25 minutes. The solvent gradient was used to elute the oligomer from the column and the fraction containing the peak was collected and lyophilized.

When gel electrophoresis was used for purification, a 1.5 mm thick denaturing polyacrylamide gel was employed. The oligomer was visualized under short wave ultraviolet light and the appropriate band was cut out and eluted from the gel pieces using 100 mM triethylammonium bicarbonate at pH 7.0 for 4 hours at 60° C. The oligomer present in the eluant was then desalted on a 1 ml disposable $C_{18}$ column (Biorad) and was eluted from the column using 25% acetonitrile in water. The DNA content was determined by measuring absorbance at 2600 Å in a 1 ml diuted aliquot, and the purified derivatized probe lyophilized.

EXAMPLE 2

Labeling Activated Probes a) Polypeptide Synthesis

A 13 residue polypeptide was synthesized on an Applied Biosystems 430A automated peptide synthesizer according to the method of Merrifield [R. B. Merrifield, "Solid Phase Peptide Synthesis I: Synthesis of a Tetrapeptide", *J. Amer. Chem. Soc.*, 85, pp. 2143–54 (1963)]. The synthetic polypeptide had the sequence:

LysTyrGlyLysAsnSerLysProArgLysGluThrCys.

Following synthesis of the polypeptide, it was deprotected using anydrous hydrogen fluoride in the presence of the scavengers para-thiocresol, paracresol and ethylmethyl sulfide. The scavengers were used in order to minimize the formation of side products. The reagents were employed in the following mixture:

10 ml 100% anyhdrous hydrogen fluoride
1 ml para-cresol
1 ml ethylmethyl sulfide
0.1 g para-thiocresol.

The crude peptide was purified by HPLC using a preparative $C_4$ or $C_{18}$ column using 0.1% trifluoroacetic acid in water as a solvent A and 0.1% trifluoracetic acid in a mixture of 20% acetonitrile and 80% water as a solvent B. A gradient of 0% of solvent B to 100% of the solvent B over 40 minutes was used to elute the peptide from the column. The purified peptide was detected by monitoring absorbance at 2200 Å. Aliquots containing the purified peptide were collected, lyophilized and stored at 4° C. The composition of the polypeptide was confirmed by hydrolying the polypeptide in 6N HCl for 24 hours at 110° C., followed by analysis of the hydrolysate on a Beckman amino acid analyzer.

b) Attachment Of Label To Probes

Approximately 1.5 $A_{260}$ units of the dried derivatized probe prepared according to Example 1 were suspended in 400 μl of 0.2M HEPES buffer at pH 7.7. To this was added 2 mg of succinimidyl 4-[N-maleimidomethyl] cyclohexane-1-carboxylate in 300 μl of acetonitrile. After mixing, the reaction was allowed to proceed for six hours at room temperature. The acetonitrile was then removed using a speed-vac. The aqueous solution, after pelleting the insoluble precipitate, was applied to a 5 ml G25 column equilibrated in 50 mM TEAA at pH 7.0, and the resulting condensate, 5'-maleimidomethyl cyclohexyl oligonucleotide, was eluted using the same buffer. Six 10 drop fractions were collected, and the fractions containing the reaction product purified using a $C_8$ column under the conditions previously described for purification of the activated probe. The reaction product was lyophilized and its DNA content determined, after resuspending it in water, by measuring its absorbance at 260 Å.

About 0.8 O.D. units (absorbance measured 260Å of reaction product in 200 μl of HEPES buffer at pH 7.3 were mixed with 2 mg of polypeptide label. The reaction was allowed to proceed for one hour. The labeled oligonucleotide was purified using HPLC under the conditions previously described for purification of the activated oligomer. The labeled probe eluted as a single peak having a lower retention time as compared to the unlabeled probe. The peak corresponding to the labeled probe was collected, lyophilized and resuspended in 1 ml of water. Its absorbance at 260µl indicated that it consisted of 0.18 O.D. units.

c) Biotinylation Of Labeled Probes

The labeled probes from part b) of this Example were lyophilized in a speed-vac. The lyophilized DNA was suspended in 200 µl of 0.2 M HEPES buffer at pH 7.3. One mg of biotin-N-hydroxysuccinimide ester was mixed with 200 µl of acetonitrile. This mixture was added to a solution of labeled probe molecule, and the reaction was permitted to proceed for 4 hours at room temperature. The acetonitrile was evaporated using a speed-vac and the aqueous solution was purified by HPLC using a $C_8$ column under the conditions described in Example 1. The biotinylated labeled probe eluted from the column as a single peak well separated from the starting material. The biotinylated labeled probe was collected, lyophilized and suspended in 1 ml of a mixture of 10% acetonitrile and water. The mixture had an absorbance of 0.1 OD unit at 260 Å.

EXAMPLE 3

Detection of DNA Sequences Using the Labeled Probe a) Preparation Of Dot Blots

Dot blots [F. C. Kafatos et al., "Determination Of Nucleic Acid Sequence Homologies And Relative Concentrations By A Dot Blot Hybridization Procedure", *Nucelic Acids Research*, 7, pp. 1541-22 (1979)]were prepared from a tPA containing plasmid, using serial dilutions of the plasmid DNA spotted on a nitrocellulose filter. Each dot also included 2 ng of sonicated salmon sperm DNA.

b) Prehybridization Treatment Of Filters

Dried filters impregnated with analyte and salmon sperm DNA were wetted in water and in 6x SSC[a] and blotted dry. The filters were then treated with the following solution for 2-4 hours at 46° C.

[a] 3.0 M sodium chloride 0.3 M sodium citrate 5 ml 100% formamide
2.5 ml 20x SSC
0.5 ml 100x SSC
0.25 ml 25 nM sodium phosphate solution (pH 6.5)
0.75 ml water The above solution was used for treatment of 4 filters.

c) Hybridization

Hybridization of the labeled probe molecule to the test sample was carried out in a buffer solution with the following composition:

4.5 ml formamide
2.5 ml 20x SSC
0.1 ml 100x Denhardts' solution[b]
0.2 ml 1M sodium phosphate at pH 6.5
0.2 mg/ml freshly boiled salmon sperm DNA
2 3 ml water Labeled probe was used at a concentration of 50 ng/ml of hybridization solution. Hybridizations were performed using 5 ml of buffer solution in a sealed hybridization bag for two filters.

[b] Denhardt et al., *Biochem. Biophys. Res. Comm.*, 23, pp. 641-45 (1966).

After hybridization, the filters were washed as follows:

6x SSC for 10 minutes at room temperature (2 changes)
3x SSC for 10 minutes at 46° C. (2 changes)
1x SSC for 10 minutes at 55° C. (2 changes)
0.1x SSC for 10 minutes at 55° C. (2 changes)

d) Filter Blocking

In order to minimize background, non-specific sites on the filters used for dot blots were blocked. Filters were washed in 0.1M Tris buffer at pH 7.5 for 5 minutes. The filters were then incubated in in 3% bovine serum albumin in a mixture of 0.1M Tris buffer and 0.45M sodium chloride at pH 7.5 for 30 minutes at 58° C., and blotted dry.

e) Detection

Bound probe was detected using the BluGene ™ Non-Radioactive Nucleic Acid Detection System (BRL). Briefly, washed and blocked filters were incubated in freshly prepared streptavidin-alkaline phosphatase conjugate solution for 15 minutes at room temperature with gentle shaking. The conjugate solution was prepared by adding 10 microliters of 1 mg/ml stock solution to 10 ml of 0.1 ml Tris buffer at pH 7.5. Ten ml of this solution was used for two filters. Following this incubation, filters were washed two times for 15 minutes each with 200 ml of Tris buffer and 0.45M sodium chloride at pH 7.5 for 15 minutes at room temperature.

For visualizing the hybridization of labeled probe molecules to sample DNA, the filters were incubated with a color development solution. The solution contained 44 µl of nitroblue tetrazolium in dimethylformamide (75 mg/ml in 70% dimethylformamide) and 33 microliters of 5-bromo-4-chloro-3-indoyl/phosphate (50 mg/ml in 100% dimethylformamide) to 10 ml 0.1M Tris buffer containing 0.45M sodium chloride and 50 mM magnesium chloride at pH 9.5. The incubation was carried out under low light for two to three hours in a sealed polypropylene bag. Color development was stopped by washing the filters in a solution consisting of 20 mM Tris buffer and 0.5 mM EDTA at pH 7.5. The filters were then blotted and dried under vacuum for two minutes prior to storage.

f) Results

When probe 1 was used for hybridization studies, 0.625 pg of target DNA could be detected visually when washes consisting of 2 changes of 6x SSC and 2 changes of 3x SSC all at 46° C. for ten minutes were used. Similar results were obtained with probes consisting of shorter polynucleotides (probes 2 and 3), under similar washing conditions. None of the probes hybridized to the control DNA. In addition, probe 3, which had a GC content of 37%, produced negligible background when compared with probes 1 and 2 which had a higher GC content.

When probe 3 was used for hybridization studies and the filters were washed under high stringency conditions (i.e., the entire wash protocol set forth in Example 3) we could still visualize 10 pg of target DNA using colorimetric detection techniques.

When probe 4, which contains a single base mismatch, was tested under the same conditions, no probe DNA could be detected. Thus, our technique is sufficiently sensitive that it is capable of detecting alteration of a single base pair.

EXAMPLE 4

Detection of DNA Sequences in Human Genomic DNA

It is also possible to use the labeled probes of this invention to detect the presence of particular nucleotide sequences in a sample of genomic DNA. In fact, as demonstrated in this example, use of the labeled probes of this invention in conjunction with the Southern blotting technique [E.M. Southern, "Detection of Specific Sequences Amoung DNA Fragments Separated By Gel Electrophoresis," *J.Mol.Biol.*, 98, pp. 503-17 (1975)] permits detection of single copy genes (i.e., nucleotide sequences which occur only once in the genome of an organism) in a sample of genomic DNA.

Three probes were synthesized and labeled as described in Example 1. The probes had the following sequences:

1. 5' GAC CAC GCT GCT CTC CTG GGC ACA GCG GGA CGA ATC CGA 5. 5' CTG GTA TAT CAT CTG CGT TTT TTC 6. 5' CTG GTA TAT CAC CTG CGT TTT TTC

Probes 1 and 5 are perfectly matched anti-sense probes to the human tPA gene and probe 6 is the same as probe 5 except at the underlined position, which is an intentionally introduced mismatch. Probe 1 of this Example is the same as probe 1 of Example 1. Probes 5 and 6 are complementary to a different region of the tPA gene.

a) Preparation Of Human Genomic DNA

Human genomic DNA was isolated from cells of the human cell line GM 1416,48,4X, obtained from the Human Genetics Mutant Cell Repository in New Jersey, by the method of R. Cate, "Comparison Of The Methylation Patterns Of The Two Rat Insulin Genes", *J. Biol. Chem.*, 258, pp. 6645-52 (1983). Aliquots of this DNA were cut with three different restriction enzymes to produce fragments of different lengths. The restriction enzymes were chosen so that they would not cut the DNA at positions within the target sequence.

For analysis with probe 1, 20 μg of human genomic DNA, prepared as above, was treated with 0.67 units of Bgl II. To monitor digestions of genomic DNA, 10 μl of the reaction mixture was removed and added to 0.6 μg of DNA isolated from λ phage. Following treatment with the restriction enzyme, the DNA was precipitated with ethanol. The fragments were then separated on a 1.0% agarose gel, using the λ DNA as a control for the performance of the restriction enzymes. Human genomic DNA from the same cell line was also digested using the enzymes Eco RI and Hind III as described above. The size of the restriction fragments that contain the target sequence of probe 1 in DNA digested with Bgl II Eco RI and Hind III was 5803, 1570 and 3390 base pairs, respectively.

For analysis with probes 5 and 6, human genomic DNA was cut with Bgl II, Pvu II and Bgl I, as described above. The sizes of the restriction fragments that included the target sequence for probes 5 and 6 were 5176, 3843 and 1510 base pairs, respectively, when analyzed on 1.0% agarose gels.

The restriction fragments of human genomic DNA were transferred to nitrocellulose filter paper or to nylon membranes according to the method of E. M. Southern (1975).

b) Analysis Of Human Genomic DNA With Probe 1

DNA impregnated nylon membranes were treated as described in parts b) through d) of Example 3 except that only the first two washes of part b) were employed and color development (part d) was allowed to proceed for only 90 minutes.

c) Analysis Of Human Genomic DNA With Probes 5 And 6

DNA impregnated nitrocellulose filters were bathed in a mixture containing 100 μg of freshly denatured salmon sperm DNA and 10 ml of plaque screen buffer (2 g polyvinylpyrrolidone, 2 g ficoll-400, 2 g bovine serum albumin, 58 g sodium chloride, 1 g sodium pyrophosphate, 10 g sodium dodecyl sulfate (SDS) and 950 ml distilled water), at 50° C. for 30 minutes. Hybridization was carried out using 40 ng of either probe in 5 ml of buffer at 50° C. overnight.

The hybridized filters were washed under high stringency conditions as follows:

a) each filter was washed separately in 100 ml plaque screen buffer at 50° C. for 15 minutes b) the filters were combined and a second wash was done with 0.1% SDS in 3x SSC at 50° C. for 15 minutes.

c) the filters were then washed in two changes of a mixture of 1.0 % SDS and 3.2 M trimethyl ammonium chloride at 60° C. for 20 minutes d) the final wash was with 0.1% SDS and 3x 15 SSC at 60° C. for 15 minutes.

Filter blocking and visualization were carried out as described in parts c) and d) of example 3, except that color development was terminated after 2 hours.

d) Results

Probes 1 and 5, which are complementary to regions of the tPA gene, detected their respective targets. Discrete bands corresponding to the target DNA bands were clearly visible on the DNA impregnated filters. Probe 1 detected restriction fragments of 5803, 1570 and 3390 base pairs on the Bgl 2, Eco RI and Hind 3 digested DNA, respectively. Probe 5 detected restriction fragments of 5176, 3843 and 1570 base pairs in the Bgl II, Pvu II, and Bgl I digested DNA, respectively. In contrast probe 6, which was mismatched to the target DNA at one position did not hybridize to any bands.

These results demonstrate that the labeled probes of this invention can discriminate between targets that differ in only a single nucleotide. It is also significant that probe 5, which was only 24 nucleotides in length and contained only 37% guanine and cytosine was effective.

EXAMPLE 5

Detection of Antigen Antibody Complexes

In another embodiment of this invention, the biotinylated peptide label is attached to antibodies specific to proteins to be detected. Alternatively, the label may be attached to an antigen, and an antibody specific thereto may be detected. In yet another embodiment, one labeled antibody may be used to detect the presence of a second antibody. And in another embodiment, the label may be attached to a protein or polypeptide which specifically binds to a receptor, the receptor not being either an antigen or antibody, as for example, a cell surface receptor for a hormone, in order to detect the presence of such receptors. In the interest of simplifying the following discusion, the term "specific binding reagent" will be used to describe that moiety to which the label is attached, it being understood that the specific binding reagent may be any proteinaceous substance which binds specifically to a substance whose presence is to be determined, that substance being defined as the target of the specific binding reagent.

Because the label preferably carries multiple bridging moieties, it is possible to attach multiple signalling moieties to each antibody molecule by way of single point of attachment between the label and the antibody.[a] In contrast, most existing methods of antibody labeling require attachment of multiple signalling moieties to each antibody molecule with corresponding risk of alterating specificity, or a "sandwich" employing second antibodies (See, e.g., U.S. Pat. 4,376,110) to achieve comparable signal intensity.

[a] Any signalling moiety may be employed. Examples of useful signalling moieties include enzymes, fluorescent compounds, radioactive isotopes, and coumarin.

Because antibody molecules have both free amino groups ($\epsilon$-amino groups of lysine and N-terminal amino groups) and cysteine residues, the chemistry for attaching the label to the antibody is preferably different from other embodiments of this invention. In the presently preferred embodiment, the peptide is first biotinylated at reactive $\epsilon$-amino, $\alpha$-amino and $\delta$-amino groups (if present). A linkage group is formed by reacting an amino and sulfhydryl reactive hetero bifunctional reagent, preferably succinimyidyl 4-[N-maleimidoethyl]-cyclohexane-1-carboxylate ("SMCC") with a sulfhydryl group, preferably at a cysteine residue of the peptide. The cysteine with which the amino and sulfhydryl reactive hetero bifunctional reagent reacts may occur at any point in the peptide, including its amino or carboxy termini. Other amino and sulfhydryl reactive hetero bifunctional reagents, such as metamaleimiobenzoyl-N-hyrdosuccinimide ester, N-succinimydyl [4-iodoacetyl]aminobenzoate, N-succinimydyl [4-bromoacetyl]and -succinimydyl 3-2-pyridylthio] propionate are also within the scope of this emodiment. Mixing the derivatized peptide and the specific binding reagent then effects covalent attachment of the derizatized label to the specific binding reagent by reaction of the amino reactive function of the amino and sulfhydryl reactive hetero bifunctional reagent with free amino groups of the specific binding reagent.

Alternatively, it is possible to attach a peptide label which includes at least one cysteine residue to a specific binding reagent that also includes at least one cysteine residue without the use of a linkage group. This is because upon mixing, cysteine residues will react with one another to form disulfide linkages between them. This reaction has relatively slow kinetics as compared with the reaction between SMCC and cysteine residues. The reaction is carried out overnight with gentle rocking at 4° C.

a) Biotinylation Of Peptide Label

Five mg. of the peptide label of Example 2 a) was was taken up in 500 $\mu$l of 0.2 M NaHCO$_3$ at pH 8.2. To this solution was added 10 mg of biotin-N-hydrosuccinimide ester in 200 $\mu$l of acetonitrile, in order to achieve a molar excess of biotin. An aliquot of 100$\mu$l of water was added to clear turbidity. The reaction was allowed to proceed for four hours at room temperature. Next, 20 mg of dithiothreitol was added to provide reducing conditions; the reaction was allowed to proceed for 16 hours. The resulting solution was desalted on a 5 ml G25 column in phosphate buffered saline ("PBS") (0.137 M NaCl, 2.7 mM KCl, 7.8 mM Na$_2$HPO$_4$·7H$_2$O and 1.47 mM KH$_2$PO$_4$). Fractions containing the biotinylated peptide were pooled. The derivitized peptide was further purified by HPLC using a C$_{18}$ column. The derivitized peptide was eluted from the C$_{18}$ column with a gradient of from 0 to 100% acetonitrile in 0.1% trifluoroacetic acid over 25 minutes. Fractions containing the derivitized peptide were collected and lyophilized.

b) Attachment Of Peptide Label To Antibody

The derivitized peptide label from part a) of this example was resuspended in 300 $\mu$l of PBS at pH 7.2. Two mg of SMCC in 50 $\mu$l of acetonitrile was added to this solution. The reaction was allowed to proceed for 1 hour. The reaction mixture was then purified by HPLC as described in part a) of this example. The derivatized peptide bound to the SMCC linkage group ("peptide") was collected and quantitated by measuring absorbance at 2710 Å.

One mg of a monoclonal antibody to lipocortin-1 was combined with 0.3 or 0.45 $\mu$g of peptide in 300 $\mu$l of PBS at pH 7.2. The reaction was allowed to proceed for 16 hours with gentle rocking at 4° C. At the end of this period, the reaction mixture was dialyzed against 1x PBS (to which had been added 0.2% sodium azide) at 4° C. with two changes of buffer. Following dialysis, the volume of the reaction mixture was increased to 1 ml with PBS and the mixture was stored cold.

c) Results

Purified lipocortin-1 was mixed with electrophoresis running buffer (50 mM Tris HCl at pH 6.8, 12.5% glycerol, 2% SDS and 2% mercaptoethanol), heated at 65° C. for 10 minutes and analyzed by SDS PAGE [Laemmli, *Nature*, 227, pp. 60-85 (1970)]. Individual lanes contained 1, 0.1, 0.01, and 0.001 $\mu$g of lipocortin-1. After electrophoresis, proteins were transferred to nitrocellulose according to the method of Towbin et al., *Proc. Nat. Acad. Sci U.S.A.*, 76, pp. 4350-54 (1979).

The nitrocellulose filters were wetted in a mixture of 10 mM Tris HCl and 150 mM NaCl ("Tris buffer") at pH 7.5 for 10 minutes. Non-specific binding sites on the filters were blocked by treating the filters with a solution of 3% bovine serum albumin ("BSA") in Tris buffer for 30 minutes at room temperature. The filters were rinsed in Tris buffer and then incubated individually, with gentle agitation, for 1 hour in 10 ml of a solution of Tris buffer containing 10 $\mu$g of antibody labeled according to parts a) and b) of this Example.

Antibody treated filters were extensively washed in about 200 ml of Tris buffer, using 3 changes of buffer for about 10 minutes per change. The filters were then incubated in 10 ml of Tris buffer containing 1.0 $\mu$g/ml of streptavidin-alkaline phosphatase conjugate (Example 3 e)) for 10 minutes. Next, the filters were washed in two changes of 150 ml Tris buffer for 10 minutes per change. For color development, the filters were incubated in a mixture of 100 mM Tris HCl, 0.45 M NaCl, and 50 mg MglC$_2$ at pH 9.5 containing 0.33 mg/ml nitroblue tetrazolium ("NBT") and 0.165 mg/ml 5bromo-4-chloro-3-indolylphosphate ("BCIP") in the dark for 2 to 3 hours. The color development was stopped by washing the filters in water. Filters treated with 0.30 $\mu$g and 0.45 $\mu$g of labeled peptide showed reaction product in the lanes loaded with as little as 10 ng of lipocortin-1.

EXAMPLE 6

Use of Chemiluminescent Substrates in Non-Isotopically Labled Oligonucleotide Hybridization Assay In yet another embodiment of this invention, a substrate for alkaline phosphatase that yields a chemiluminescent product is employed in place of nitroblue tetrazolium ("NBT") and 5-bromo-4-chloro-3-indolylphosphate ("BCIP") substrate of examples 3 and 5. In one embodiment a dioxetane having the formula:

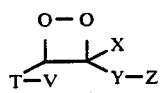

is used as a substrate for alkaline phosphatase. In this embodiment, T is a cycloalkyl or polycycloalkyl group bonded to the 4 membered ring by a spiro linkage; V is H or an enzyme cleavable group; Y is a fluorescent chromophore; X is H, alkyl, aryl, aralkyl; alkaryl, heteroalkyl, heteroaryl, cycloalkyl, cycloheteroalkyl, or enzyme cleavable group, and Z is H or an enzyme cleavable group, provided that at least one of V, X, Y or Z must be an enzyme cleavable group, so that the enzyme cleaves the enzyme-cleavable group from the dioxetane to form an unstable negatively charged species that further decomposes releasing the chemical bonding energy of dioxetane as light. More preferably this substrate is 3-(2'-spiroadamantane)-4-methoxy-4-(3'-phosphoryloxy)phenyl-1,2-dioxetane ("AMPPD"). High energy chemiluminescent substrates such as AMPPD permit faster analysis and more sensitive detection of binding between probe and analyte. Cleavage of AMPPD by alkaline phosphatase yields a chemiluminescent species which can be detected by optical instrumentation. See EPO applications 254,051 and WP 88/00695. Although the results presented in this example are based on use of AMPPD with a DNA probe, the methodology presented may be also employed in connection with the specific binding reagent disclosed in Example 5. Additionally, it should be understood that any other combination of enzyme and substrate compound which produces a chemiluminescent species upon reaction between the enzyme and substrate is within the scope of this embodiment.

a) Preparation of Samples

Southern blots of human genomic DNA were prepared according to the procedure of Example 4a). Aliquots of 20 μg of DNA were digested with the restriction endonucleases Bgl2, EcoR1 and Hind3 to generate fragments of 5803, 1570 and 3390 base pairs respectively as in Example 4a). The digested DNA was subjected to electrophoresis on a 1% agarose gel. After denaturation and neutralization, the DNA fragments were transferred to nylon membranes also as described in Example 4a).

DNA probes identical to Probe 1 of Example 4 were hybridized to the genomic DNA according to the protocol described in Example 3b) and c), except that the probes were used at a concentration of 8 ng/ml of the hybridization solution. The filters were then washed and blocked, also according to the protocol disclosed in Examples 3c) and d).

b) Preparation Of Substrate

The alkaline phosphatase substrate AMPPD may be produced by synthesizing the olefinic intermediate

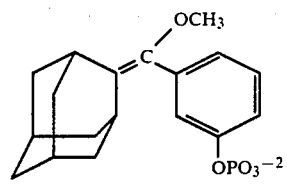

This intermediate is synthesized by the reaction of spiroadamantanone and a phosphorous ylide. The phosphorous ylide is formed by the reaction of triphenyl phosphine and the brominated benzene derivative:

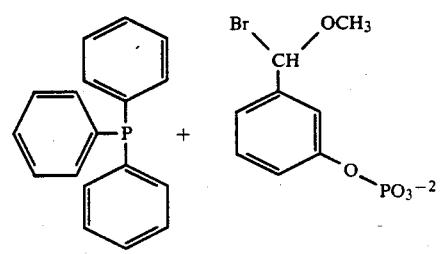

in the presence of the strong base, n-butyl lithium, at −78° C. in tetrahydrofurane to yield a phosphorous ylide;

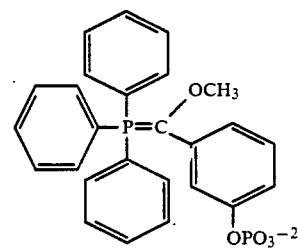

This ylide, upon reaction with spiroadamantanone yields the olefinic intermediate A.

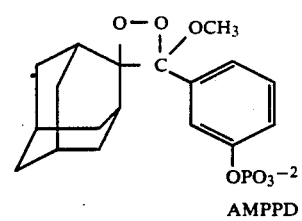

AMPPD

Irradiation of the olefinic intermediate A in the presence of singlet oxygen yields AMPPD.

b) Detection

The performance of NBT/BCIP and AMPPD as substrates for alkaline phosphatase was evaluated by comparing the results obtained with these substrates on otherwise identically treated filters. One filter was treated as described in Example 3e). A second filter, after blocking with 3% w/v BSA in a solution of 0.1M Tris HCl and 0.45 NaCl at pH 7.5, was incubated with streptavidin-alkaline phosphatase solution (0.1 mg/ml in Tris buffer as described in Example 3e)) for 15 minutes at room temperature. Following incubation, the filter was washed in two changes of 150 ml of a solution of 0.1M Tris HCl and 0.45 NaCl for 15 minutes at room temperature.

The membranes were washed in a solution consisting of 0.1% BSA, 5 mM NaHCO$_3$, and 1 mM MgCl$_2$, at pH 9.5. After washing, the membrane was saturated with 100 μl of 1.6 mM AMPPD in 0.1% BSA, 5 mM NaHCO$_3$, and 1 mM MgCl$_2$ at pH 9.5. The membrane was sealed in a plastic pouch and placed in a camera luminometer where light emission was imaged on Polaroid Instant Film (ASA 20,000). Membranes treated with NBT/BCIP substrates produced detectable signals in 30 minutes, whereas the AMPPD produced detectable signals within 2 minutes. Additionally, the chemiluminescent product permits a more sensitive assay than with conventional NBT/BCIP technology. It should be understood that other detectors of chemiluminescence may be used in place of the photographic film of this example. Such detectors include video equipment and solid state photon detectors.

EXAMPLE 7

Non-Radioactive Detection of Target Genes in Human Genomic DNA Using PCR Technology Polymerase Chain Reaction technology ("PCR") is being used increasingly in various aspects of molecular biology, including medica diagnostics. The methodology provides for detection of target sequences from very small amounts of DNA isolated from cells or tissues. This embodiment discloses a method for rapid and sensitive detection of target sequences employing PCR. Also within the scope of this embodiment is a rapid method for preparation of DNA samples from blood for PCR.

Briefly, PCR is a method for amplifying a target nucleotide sequence by causing a heat stable DNA polymerase and oligonucleotide primers to generate DNA extension products from nucleotide monomers, beginning from a site at which primers bind to complementary polynucleotide strand templates. The primers are selected so that they bracket the sequence to be amplified. Following generation of fragments from the template strand, elevation of the temperature of the reaction medium causes the dissociation of the template strands, the heat stable DNA polymerase and the extension fragments without inactivating the DNA polymerase enzyme. In a preferred embodiment, the heat stable DNA polymerase is derived from *Thermus aquaticus*. Each extension product can then serve as a template for another round of synthesis, thus amplifying the amount of sequence sought exponentially. See generally EPO Application 258,017.

The probe labelling and sample preparation methodology of this invention can be combined with PCR to provide a powerful technique for detection of target sequences. In this Example these embodiments are employed in the detection of the tPA gene in human genomic DNA.

a) DNA Isolation From Cells Suspended In Fluids For PCR

An aliquot of 50 μl of human blood was mixed with 200 μl of a cold solution of 0.15 M NaCl and 50 mM Tris HCl at pH 7.5. The solution was mixed at low speed using a laboratory vortex mixer. The cells were then spun down by centrifugation at about 5,000 rpm for 1 minute. After discarding the supernatant, the cells were washed by resuspending the cells in the above buffer and repeating the mixing and centrifugation steps.

The pelleted cells were then treated with 100 μl of NP40 in 1x PBS (any other nonionic detergent may be employed in place of NP40) at 4° C. The mixture was vortexed briefly, and the nuclei were spun down by centrifugation at 5,000 rpm for 1 minute. The supernatant was gently removed by pipetting. The nuclei were washed by adding 100 μl of a cold solution of 0.15 M NaCl and 50mM Tris HCl at pH 7.5. The liquid was again gently removed by pipetting.

Next, 10 μl of 1% sodium deoxycholate (any negatively charged detergent may be used in place of sodium Deoxycholate[a]) was added to the nuclear pellet. The mixture was vortexed and centrifuged as before. The solution was allowed to stand for 15 minutes at room temperature. The solution was then boiled for 5 minutes to solubilize the DNA, and again vortexed and centrifuged. An aliquot of 10 μl of double distilled water was added to the DNA solution, and 10 μl of the resulting solution was used for the remainder of this example. The resulting DNA solution was diluted to 500 μl with a mixture of 10 mM Tris HCl and 1 mM EDTA (ethylene diamine tetraacetic acid) at pH 7.5, vortexed and centrifuged as before. 50 μl of this solution was used as a source of human DNA for PCR. It will also be apparent that although this Example employs small amounts of human blood as a sample, this technique may be applied to other cell suspensions, as well as to larger or smaller volumes. For example, this technique may also be used to study nucleic acids from cells grown in culture, or to a sample of synovial fluid.

[a] Sodium ions may be a dodecylbenzene sulfonate (also known as sodium dodecyl sulfate) at 1% concentrations may be used in place of sodium deoxycholate for nuclear lysis. If so, it must be removed using C$_{18}$ silicasolid support (Whatman), prior to amplification with PCR. Companion experiments done with this detergent yielded results comparable to those with sodium deoxycholate.

Although it is preferred to employ this method for isolation of DNA in the preparation of samples for PCR, it is also within the scope of this embodiment to employ the method for preparation of DNA for other purposes.

b) Amplification Of Target Sequences In Human Genomic DNA

Two primers were synthesized using the methods disclosed in Example 1 *a*). The primers had the sequence:

Primer A: 5' AAA GTG CTG GGA TTA CCA GC 3'
Primer B: 5' TGG CCT CCT AAA GTG CTG GG 3'

Primer A is complementary to the +strand coding for tPA and Primer B is complementary to the corresponding strand. Use of these primers results in amplification of a 350 base pair DNA fragment.

The PCR reaction was carried out in the following reaction mixture:

| | |
|---|---|
| 10x buffer | 10 μl[a] |
| human DNA | 10 μl[b] |
| double distilled H$_2$O | 53.5 μl |
| deoxynucleotide triphsophates | 16.0 μl[c] |
| Primer A | 5.0 μl[d] |
| Primer B | 5.0 μl[d] |

| -continued | |
|---|---|
| Taq polymerase | 0.5 μl[e] |

[a]The PCR reaction buffer consists of 500 mM KCl, 100 mM Tris HCl, 15 mM MgCl₂ and 0.1% w/v gelatine at pH 8.3.
[b]Paired experiments were carried out using human DNA prepared according to part a) of this example and with human DNA prepared according to conventional technology. See, e.g. P. E. Devlin et al. "Southern Analysis Of Genomic DNA with Unique and Degenerate Oligonucleotide Probes: A Method for Reducing Degeneracy," DNA, 1, pp. 499–507 (1988). When the source of human DNA was human blood, treated according to part a) of this Example, 50 μl of the final solution was used for the PCR reaction mixture. The volume of double distilled H₂O in that reaction mixture was correspondingly reduced by 40 μl to 13.5 μl.
[c]A mixture of the 4 deoxynucleotides normally present in human cells (i.e., dATP, dGTP, dCTP and dTTP) each present at a concentration of 200 μM was used.
[d]At a concentration of 1 μM
[e]corresponds to 2.5 units. The Taq polymerase enzyme was obtained from Perkin Elmer-Cetus; the volume indicated in the text was used from the material supplied.

Each PCR cycle consisted of the following steps:
1. denaturation for 2 minutes at 93° C.
2. primer annealing for 2 minutes at 40° C.
3. chain extension for 4 minutes at 60° C.

These three steps were carried out for a total of 40 cycles in a Perkin-Elmer-Cetus Thermocycler. The initial mass of human genomic DNA in the PCR reaction mixture was 100 ng., 10 ng., 1 ng., and 0.1 ng for each of 4 separate experiments.

c) Detection

After completion of the above steps, 10 μl of the reaction mixture was denatured at 60° C. for in 15 μl of a mixture of 0.5 M NaOH and 1.5 M NaCl. After 1 hour, the mixture was neutralized with 200 μl of 0.5 M Tris and 1.5 M NaCl at pH 7.5. Samples were blotted onto nitrocellulose filters using a slot blotting apparatus Minifold 2 Slot Blotter, Sshleicher & Schuell].

Filters were hybridized in 10 ml of PBS containing 100 μg/ml of sonicated salmon sperm DNA and 8 ng of a probe with the sequence of probe 6 in Example 4 at 55° C. overnight. the filters were washed in the following solution:

5x SSC[f] and 0.1% SDS at 55° C. for 10 minutes (2 changes)
3x SSC and 0.1% SDS at 50° C. for 10 m
1x SSC and 0.1% SDS at 50° C. for 10 minutes (2 changes)

After washing the filters, nonspecific binding sites on the filters were blocked according to the procedure of Example 3d). Bound probe was detected according to the method of Example 3e).

Additionally, after completion of the PCR reactions, 10 μl from each of the four experiments was subjected to agaraose gel electrophoresis according to method of Example 4 except that a 2% agarose gel was used. Following denaturation and neutralization the DNA was transferred onto nitrocellulose or Gene-screen ™ filters also as described in Example 4. The filters were washed, blocked and the bound probe detected also as described in Example 4 using probes with the sequence of probe 6 of that Example.

d) Results

The combination of PCR and probe labeling allowed detection of target sequence in as little as 100 pg of starting genomic DNA following electrophoresis and Southern blotting of the product of the PCR reaction. This corresponds to roughly 30 molecules of DNA in the PCR reaction mixture. We confirmed that the DNA fragment detected was the 350 base pair fragment amplified by PCR by Southern blotting the DNA fragments after separation by agarose gel electrophoresis. The 350 base pair amplified fragment was also detected when the human DNA was prepared according to part a) of this example. In that case a gene was detected in the equivalent of 0.625 μl of human blood.

EXAMPLE 8

Use of Labeling in Antisense Therapy

Antisense therapy refers to the administration of exogenous polynucleotides which bind to target polynucleotides located within cells. The term "antisense" refers to the fact that such oligonucleotides are complementary to their intracellular targets. Useful oligonucleotide sequences interfere with or modulate the processes of growth and replication. It is believed that this methodology will permit development of novel antiviral and antineoplastic pharmaceutical agents. See "Antisense Molecular Biology and 'S-oligos'", Synthesis, 1, pp. 1–5 (Synthecell, October 1988) for a general review.

A major obstacle in the development of useful antisense therapeutic agents has been the intracellular location of their targets. Id. See also, LeMaitre, et al. "Specific Antiviral Activity Of A Poly(L-lysine))-Conjugated Oligodeoxyribonucleotide Sequence Complementary to Vesicular Stomatitis Virus N Protein mRNA Initiation Site", Proc. Nat. Acad. Sci. U.S.A., 84, pp. 648–52, 648 (1987). Accordingly, it is desirable to develop a method for intracellular delivery of such agents.

In one embodiment of the present invention, antisense therapeutic agents ("antisense agents") are bound to a peptide that is ingested by cells ("peptidyl antisense agent"). Examples of useful peptides include peptide hormones, antigens or antibodies, and peptide toxins. By choosing a peptide that is selectively taken up by a group of cells or a tissue that is to be exposed to the antisense agent, specific delivery of the antisense agent may be effected.

The antisense agent is covalently bound to a peptide, that is known to be ingested by cells, according to the method of Examples 1 and 2. Briefly, the 5'—OH group of the antisense agent is activated by aminoalkylation. A peptide is covalently attached to the activated antisense agent by an amino and sulfhydryl reactive hetero bifunctional reagent. The latter is bound to a cysteine residue present in the peptide.

Upon exposure of cells to the antisense agent bound to a peptide, the peptidyl antisense agents are endocytosed, and the antisense agent binds to target polynucleotides within the cells, thus exerting its therapeutic effect.

While we have hereinbefore presented a number of embodiments of this invention, it is apparent that our basic construction can be altered to provide other embodiments which utilize the processes and compositions of this invention. Therefore it will be appreciated that the scope of this invention is to be defined by the claims appended hereto rather than by the specific embodiments which have been presented by way of example.

We claim:

1. A labeled probe comprising a polynucleotide sequence complementary to a target polynucleotide sequence, a label, including aterminal cysteine residue, and a linkage group, the label and linkage group not interfering substantially with the characteristic ability of the probe polynucleotide sequence to hybridize to the target polynucleotide sequence, the label being covalently attached to the linkage group through a sulfur-carbon single bond, the sulfur atom of which is part of the terminal cysteine residue of the label, and the linkage group being covalently attached to the polynucleotide sequence through a carbon-oxygen single bond.

2. The labeled probe of claim 1, wherein the label comprises a polypeptide, including a terminal cysteine residue.

3. The labeled probe of claim 1, wherein at least one signalling moiety is attached to the label.

4. The labeled probe of claim 3, wherein at least one signalling moiety is attached to the label by way of at least one bridging moiety.

5. The labeled probe of claim 4, wherein the bridging moiety is selected from the group consisting of biotin, iminobiotin, avidin, streptavidin and an antibody to the label.

6. The labeled probe of claim 3, 4 or 5, wherein the signalling moiety is selected from the group consisting of radioactive isotopes, enzymes, coumarin, and fluorescent compounds.

7. The labeled probe of claim 1, 2, 3 or 4 wherein the linkage group is attached at the 5' terminus of the polynucleotide.

* * * * *